(12) United States Patent
Dumas

(10) Patent No.: US 7,279,604 B2
(45) Date of Patent: Oct. 9, 2007

(54) BORON CARBIDE AS AN EFFECTIVE FRIEDEL-CRAFTS TYPE CATALYST

(75) Inventor: Philip Edward Dumas, Morrisville, PA (US)

(73) Assignee: The College of N.J., Ewing, NJ (US)

( * ) Notice: Subject to any disclaimer, the term of this patent is extended or adjusted under 35 U.S.C. 154(b) by 0 days.

(21) Appl. No.: 11/442,716

(22) Filed: May 30, 2006

(65) Prior Publication Data

US 2006/0281940 A1    Dec. 14, 2006

Related U.S. Application Data

(60) Provisional application No. 60/685,625, filed on May 31, 2005.

(51) Int. Cl.
*C07C 49/76* (2006.01)
*C07C 45/00* (2006.01)

(52) U.S. Cl. .............. 568/332; 568/323; 568/338
(58) Field of Classification Search .............. 568/323, 568/332, 338

See application file for complete search history.

(56) References Cited

U.S. PATENT DOCUMENTS

| | | |
|---|---|---|
| 4,414,406 A | 11/1983 | Fields |
| 4,547,605 A | 10/1985 | Kresge |
| 4,717,780 A | 1/1988 | Olson |
| 5,750,455 A | 5/1998 | Chauvin |
| 6,184,418 B1 | 2/2001 | Dubac |

*Primary Examiner*—J. Parsa

(57) ABSTRACT

The compound boron carbide, $B_4C$, is an effective catalyst for the alkylation and acylation of aromatics to produce polybenzyls, ketones, esters and alkyl benzenes. The catalyst boron carbide is also effective in conducting intramolecular Friedel-Crafts type reactions to produce cyclic ketones.

3 Claims, No Drawings

BORON CARBIDE AS AN EFFECTIVE FRIEDEL-CRAFTS TYPE CATALYST

CROSS REFERENCED TO RELATED APPLICATION

Provisional application previously filed. Provisional application number is 60/685,625 filed on May 31, 2005, and confirmation is No. 2470.

BACKGROUND

Friedel-Crafts alkylation and acylation reactions of organic compounds have been commonly performed with Lewis acid catalysts. However, the use of Lewis acid catalysts in commercial practice has presented problems of the catalyst being corrosive, difficult to recover and the generation of hazardous waste.

Examples of such reactions are described in the text by P. Bruice, Organic Chemistry, $4^{th}$ edition, Prentice Hall, 2004, pg. 612 and following. A common catalyst employed in both alkylation and acylation reactions is the Lewis acid, $AlCl_3$. Although $AlCl_3$ is referred to as a catalyst in the true sense, it is not. It requires stoichiometric amounts of $AlCl_3$ since it actually forms a complex with the reactant, that subsequently requires its removal from the reaction mixture by either an acid or base hydrolysis. Such a procedure is costly and, in the process toxic waste is generated which must be disposed of. Other Lewis acid catalysts have been investigated which include zeolites as disclosed in U.S. Pat. Nos. 4,547,605 and 4,717,780. Although the zeolites are effective Lewis acid catalysts, their use is often limited by the pore size of the zeolite which inhibit large sterically hindered molecules from reaching the active site within the zeolite.

Numerous Lewis acid catalysts have been disclosed which include both transition and non-transition metals as disclosed in U.S. Pat. Nos. 4,414,406 and 6,184,418, however often the catalysts are difficult to prepare or exhibit chemical reactivity that limits their use. Other disclosures include the utilization of mixed catalysts as described in U.S. Pat. No. 5,750,455.

Although much effort has been made to develop more effective catalysts for both alkylation and acylation of organic compounds there is a need for more effective catalysts that do not have the inherent problems of the ones currently employed. An ideal catalyst would be one that functions as a heterogenous catalyst, easily removed from the reactants and products, chemically and thermally stable, and readily available or easily prepared.

SUMMARY OF THE INVENTION

I have discovered that boron carbide, $B_4C$ is an effective catalyst for both alkylation and acylation Friedel-Crafts type reactions. It is readily available, chemically and thermally stable, requires no pretreatment and easily recoverable from the reactants and reaction products.

Since $B_4C$ functions as a heterogenous catalyst and is non-toxic, no hazardous waste is generated at the conclusion of the reaction. The use of $B_4C$ requires no time consuming work up at the end of the reaction, and can be reused without any regeneration or activation procedures. This discovery is unexpected since $B_4C$ is regarded in the literature as a compound that is essentially unreactive.

DETAILED DESCRIPTION OF THE INVENTION

The current literature teaches that catalysts for Friedel-Crafts reactions are classified as Lewis acid catalysts. Although many materials have been investigated as Friedel-Crafts catalysts they are all recognized as Lewis acid type catalysts. These include zeolites, clays, heteropoly acids and various metal halides.

I have discovered that the non-metal carbide, boron carbide, $B_4C$ can function as a catalyst in aklylation and acylation of aromatic compounds, previously conducted by Lewis acid Friedel-Crafts type catalysts. This is unexpected since boron carbide is regarded as a compound that has a high resistance to chemical attack.

Boron carbide is an extremely hard material whose melting point is 2450° C. It is commonly used as an abrasive in lapping application and as a refractory. It is also known to be a neutron absorber and is used in the nuclear industry. There are no reports in the chemical literature that boron carbide exhibits any chemical or physical properties which would indicate that it would function as a catalyst. This unexpected discovery is surprising in regard to the teachings in the prior art.

I have discovered that boron carbide is suitable for the alkylation of aromatics to produce polybenzyls. The rate of the reaction depends on both the amount of boron carbide present, its particle size and the temperature the reaction is conducted. The reactions are carried out by contacting the corresponding aromatic halide in the presence of the boron carbide, and these reactions proceed to completion at temperatures ranging from 80° to 160° C.

This reaction can easily be observed by heating 20 ml of benzyl chloride to about 120° C. in an evaporating dish. At the end of an hour no observable reaction has taken place. If, at this point, 0.10 gm of boron carbide is added to the benzyl chloride within minutes copious amounts of HCl is evolved and the benzyl chloride is transformed into a dark viscous mass, which is the polybenzyl product.

This novel catalyst, boron carbide is also suitable for the production of ketones by the reaction of acyl halides with aromatics. Benzophenone and substituted benzophenones were produced in high yields using boron carbide as the catalyst. At the conclusion of the experiment, the catalyst is easily recovered by filtration.

This novel catalyst was also employed to produce alkyl benzenes by reacting benzyl chloride with benzene and alkyl substituted benzenes.

Similarly boron carbide catalyzed the reaction of acyl haldides and phenols to produce the corresponding esters. High yields of phenyl benzoate were obtained by reacting benzoyl chloride with phenol in the presence of the powdered boron carbide catalyst.

The boron carbide catalyst is also useful in conducting intra-molecular Friedel Crafts type reactions in the synthesis of cylic ketones. When a solution of hydrocinnamoyl chloride in pentane is refluxed in the presence of boron carbide, the cyclic ketone 1-indanone is obtained.

The following examples illustrate the embodiments of this invention, however, it is understood, that they are presented only for illustrative purposes and do not limit the scope of this invention.

EXAMPLE 1

A mixture of 12.6 gm (0.1 mole) benzyl chloride and 0.1 gm of boron carbide was heated in an evaporating dish, with continuous stirring to 120° C. Initially copious amounts of HCl gas were evolved, ceasing in about two hours. The viscous mixture solidified upon cooling. The solid material was dissolved in benzene and the catalyst was removed by filtration. The benzene was then removed at reduced pressure and the remaining viscous material was identified as polybenzyl from its infrared and NMR spectra.

EXAMPLE 2

A mixture of 7.0 gm (0.05 mole) of benzoyl chloride and 4.7 gm (0.05 moles) of phenol and 0.1 gm of boron carbide was heated to about 60° C. for 12 hours. The semi-solid material was allowed to cool to room temperature. A solid material was recovered and dissolved in acetone, filtered to remove the boron carbide catalyst. The acetone was removed at reduced pressure and the remaining solid was identified as phenyl benzoate by its infrared spectra. The yield of product was 93%.

EXAMPLE 3

A mixture of 5.4 gm (0.05 moles) of anisole and 9.3 gm (0.05 moles) of benzoyl bromide and 0.5 gm of boron carbide was added to 50 ml of benzene. This mixture was placed in a round bottom flask fitted with a condenser and heated to reflux temperature for 12 hours with vigorous stirring. The mixture was allowed to cool to room temperature, and filtered to remove the boron carbide. Sodium hydrogen carbonate was added to remove any excess benzoyl bromide. The benzene was then removed at reduced pressure and the remaining solid was identified as p-methoxybenzophenone. The yield was 51.5% and 0.5 gm of the boron carbide catalyst was recovered.

EXAMPLE 4

A mixture of 5.4 gm (0.05 moles) of anisole and 7.0 gm (0.05) moles of benzoyl chloride and 0.5 gm of boron carbide was placed in 50 ml of benzene. This mixture was allowed to react as described in Example 3. A yield of 48.2% of p-methoxy benzophenone was obtained, and 0.5 gm of the boron carbide catalysts was recovered.

EXAMPLE 5

A mixture of 2.4 gm (0.02 moles) of mesitylene and 2.8 gm (0.02 moles) of benzoyl chloride in 50 ml of benzene containing 0.1 gm of boron carbide was allowed to reflux for 24 hours. Upon cooling, the benzene was removed at reduced pressure. The remaining solid was dissolved in an ethanol-acetone mixture and filtered to remove the boron carbide. The filtrate was allowed to evaporate to dryness and the crystals that formed were identified by its infrared spectra as 2,4,6-trimethylbenzophenone.

EXAMPLE 6

A mixture of 7.4 gm (0.04 moles) of benzyl bromide and 0.2 gm of boron carbide in 175 ml of benzene was refluxed for 24 hours. The solution was allowed to cool and filtered to remove the boron carbide. The benzene was removed at reduced pressure and 5.4 gm of a solid product was recovered. It was identified as diphenylmethane by its infrared and NMR spectra.

EXAMPLE 7

To a mixture of 3.0 gm (0.02 moles) of hydrocinnamoyl chloride and 40 ml of benzene 0.1 gm of boron carbide was added. This solution as allowed to reflux for 24 hours. At the need of this period, a sample was injected into the GC mass spectrometer. The results confirmed that the product 1-indanone was present in 15% yield.

The invention claimed is:

1. A process for the production of para-methoxybenzophenone by reacting benzoyl chloride or benzoyl bromide and anisole in the presence of the catalyst boron carbide at a temperature of 40° to 120° C.

2. A process in claim 1 in which the anisole is an alkyl substituted anisole.

3. A process for the production of a cyclic ketone by reacting hydrocinnamoyl chloride in benzene in the presence of the boron carbide catalysts at temperatures of 60° C. to 80° C.

* * * * *